US008540945B2

(12) United States Patent
Ito et al.

(10) Patent No.: US 8,540,945 B2
(45) Date of Patent: Sep. 24, 2013

(54) WATER ABSORBING MATERIAL AND MANUFACTURING METHOD THEREFOR

(71) Applicants: Hiroshi Ito, Tokyo (JP); Shinobu Hatanaka, Tokyo (JP); Takahiro Hosoya, Tokyo (JP)

(72) Inventors: Hiroshi Ito, Tokyo (JP); Shinobu Hatanaka, Tokyo (JP); Takahiro Hosoya, Tokyo (JP)

(73) Assignee: Daiki Co., Ltd., Tokyo (JP)

( * ) Notice: Subject to any disclaimer, the term of this patent is extended or adjusted under 35 U.S.C. 154(b) by 0 days.

(21) Appl. No.: 13/632,555

(22) Filed: Oct. 1, 2012

(65) Prior Publication Data

US 2013/0029040 A1 Jan. 31, 2013

Related U.S. Application Data

(60) Division of application No. 13/477,278, filed on May 22, 2012, which is a continuation of application No. PCT/JP2011/050649, filed on Jan. 17, 2011.

(30) Foreign Application Priority Data

Feb. 25, 2010 (JP) ................................ 2010-041057

(51) Int. Cl.
*G01N 33/50* (2006.01)

(52) U.S. Cl.
USPC ............................ 422/421; 436/164; 436/169

(58) Field of Classification Search
USPC .................................. 422/421; 436/164, 169
See application file for complete search history.

(56) References Cited

U.S. PATENT DOCUMENTS 5,823,139 A * 10/1998 Ito ................................ 119/171
2008/0022940 A1 1/2008 Kirsch et al.

FOREIGN PATENT DOCUMENTS

JP 2000-333547 A 12/2000
JP 2005-021071 * 1/2005

OTHER PUBLICATIONS

International Search Report issued in PCT/JP2011/050649 dated Feb. 22, 2011.

* cited by examiner

*Primary Examiner* — Monique Cole
(74) *Attorney, Agent, or Firm* — Novak Druce Connolly Bove + Quigg LLP

(57) ABSTRACT

Provided is a water absorbing material having a granular core portion and a coating layer portion coating the granular core portion, which does not produce color before use and with which a test result can be determined only after use. In the water absorbing material, the coating layer portion is composed of 90 wt % to 96 wt % of a substrate and 10 wt % to 4 wt % of an excretion test material, the excretion test material contains a porous adsorbent having an adsorbance of 25 wt % or greater and including micropores, and an excretion test indicator adsorbed on the micropores of the porous adsorbent, and the excretion test indicator is added in an amount in the range of 0.015 wt % to 0.10 wt % relative to the total amount of the coating layer portion.

7 Claims, 1 Drawing Sheet

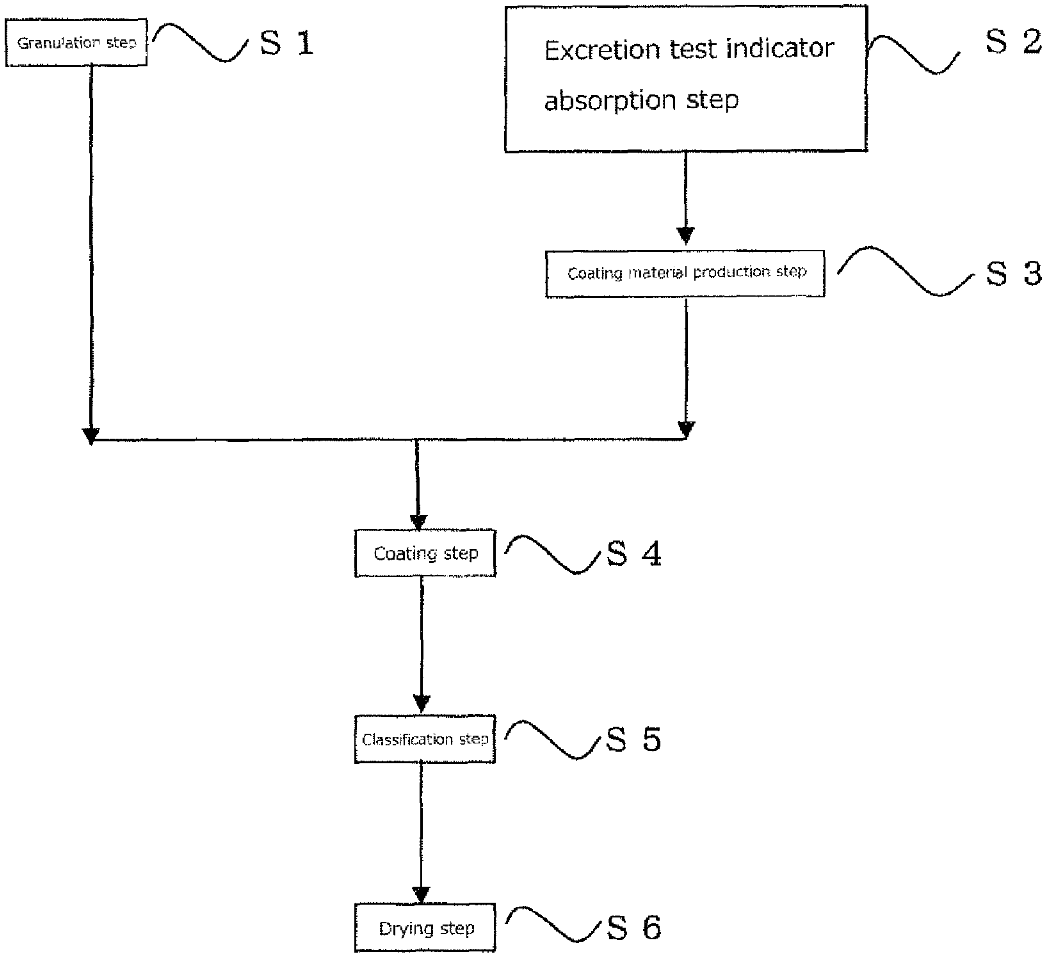
Granulation step
S 1
Excretion test indicator absorption step
S 2
Coating material production step
S 3
Coating step
S 4
Classification step
S 5
Drying step
S 6

WATER ABSORBING MATERIAL AND MANUFACTURING METHOD THEREFOR

CROSS REFERENCE TO RELATED APPLICATION

This application is a divisional application of U.S. continuation application, Ser. No. 13/477,278, filed on May 22, 2012, under 35 USC 111(a), which claimed benefit under 35 USC 120 and 365(c) of PCT application PCT/JP2011/050649, filed on Jan. 17, 2011, which in turn claimed priority to Japanese Patent Application No. 2010-041057, filed on Feb. 25, 2010, the entire contents of which are incorporated herein by reference.

TECHNICAL FIELD

The present invention relates to a granular water absorbing material having a function to test urine in fluids such as excretions of humans or animals (hereinafter simply referred to as a "water absorbing material"), and a production method therefor.

BACKGROUND ART

Recently, the number of people who like pets and like animals has been increasing, and many pet owners pay attention to pet health just like human health. There is a limit to checking a change of the health condition of a pet by observation of pet's appearance, and therefore, in order to readily discover such a change of the condition at an early stage, an excretion treating material formed in a granular shape and containing a pH indicator has been used (Patent Literature 1).

CITATION LIST

Patent Literature

[PLT 1]
JP 2000-333547A

SUMMARY OF INVENTION

Technical Problem

However, since this excretion treating material is produced by dissolving an ink composition containing a pH indicator in water and spraying the diluted solution thereof onto the surface of the excretion treating material formed in a granular shape, the excretion treating material is problematic in that, depending on the type of pH indicator, it may produce color before use due to reaction with moisture present in air or in the materials constituting the granular treating material.

The present invention was accomplished to solve the foregoing problem, and an object thereof is to provide a water absorbing material with which color production before use can be prevented and which can be inexpensively and readily produced, and a production method therefor.

Solution to Problem

To solve the foregoing problem, the water absorbing material of the present invention is a water absorbing material including a granular core portion and a coating layer portion coating the granular core portion, the coating layer portion is composed of 90 wt % to 96 wt % of a substrate and 10 wt % to 4 wt % of an excretion test material, the excretion test material contains a porous adsorbent having an absorbance of 25 wt % or greater and including micropores, and an excretion test indicator (hereinafter referred to as a "test indicator") adsorbed on the micropores of the porous adsorbent, and the test indicator is added in an amount in the range of 0.015 wt % to 0.10 wt % relative to the total amount of the coating layer portion.

Here, it is necessary to allow the aforementioned test indicator to be adsorbed on the porous adsorbent, and therefore, although the adsorption method is not particularly specified, it is preferable that the test indicator is fixed while being in a solvent-dissolved state (in particular, fixed as an ink composition).

Also, the test indicator is a reagent of any type that changes its color upon reaction with excretion such as urine, and it is thus possible to perceive a change of health condition or the like. Urinary pH value detection indicators for detecting a urinary pH value (hereinafter referred to as "urinary pH value test indicators"), urinary glucose detection indicators, urinary protein detection indicators, urinary occult blood detection indicators, urinary urobilinogen detection indicators, and like known indicators are usable.

Moreover, the water absorbing material of the present invention can be produced according to a method for producing a multi-layer water absorbing material having a granular core portion and a coating layer portion that coats the granular core portion and contains an excretion test indicator. The production method includes a granulation step of producing the granular core portion, an excretion test indicator adsorption step of dissolving the test indicator in a solvent and allowing the dissolved test indicator to be adsorbed on a porous adsorbent, a coating material production step of adding the test indicator adsorbed on the porous adsorbent to a substrate to produce a coating material that constitutes the coating layer portion, and a coating step of coating a periphery of the granular core portion with the coating material.

Regarding the water absorbing material of the present invention, a test indicator is not directly added, but the test indicator is adsorbed on a porous adsorbent. The porous adsorbent has the test indicator adsorbed in its gap portions, and therefore, leaching of moisture from the granular core portion or the like can be blocked to some extent, and if apertures are present in the gap portions, the gap portions can retain moisture. Therefore, it is possible to prevent the highly reactive test indicator from producing color, which is caused by the reaction of the test indicator, before use.

Since the test indicator is blended in the coating layer portion, the coating layer portion promptly undergoes color change because it is in contact with the test indicator, and it is thereby possible to readily determine a test result in a short period of time.

Advantageous Effects of Invention

According to the present invention, it is possible to provide a water absorbing material that does not produce color before use and with which a test result can be determined only after use, and to produce a water absorbing material inexpensively and readily.

BRIEF DESCRIPTION OF DRAWING

FIG. 1 is a flowchart showing the method for producing a water absorbing material of the present invention.

DESCRIPTION OF EMBODIMENTS

One aspect (hereinafter referred to as an "embodiment") of carrying out the present invention will now be described in detail in reference to the drawing, using as an example of a granular multi-layer water absorbing material for treating excretion (urine treating material) for a pet such as a cat or a dog.

The test indicator is described using a urinary pH value test indicator as an example.

[Water Absorbing Material]

The water absorbing material of the present invention (hereinafter referred to as the "present water absorbing material") has a multi-layer structure composed of a granular core portion for absorbing moisture from outside and a coating layer portion having a specific thickness and coating the surface of the granular core portion.

(1) Granular Core Portion

It is sufficient that the granular core portion is formed in a pellet shape, and the granular core portion does not have to be, for example, perfectly spherical. The shape thereof is not limited to columnar (elongated), flat, or the like.

The granular core portion has water absorbability or water retainability, and the materials and other features thereof are not limited as long as a substance that inhibits testing when carrying out testing of excretion (for example, in the case where a change of the pH value of excretion is to be observed, a substance that prevents pH change) is not contained.

Usable examples include virgin pulp, toilet paper wastes, tissue paper wastes, facial paper wastes, cleaning paper wastes, cellulose wadding wastes, paper towel wastes, non-woven-fabric wastes, and like organic wastes that do not inhibit testing of a pH value.

Also, bentonite, zeolite, titanium oxide, and such inorganic materials as well as other materials can be used for the granular core portion.

It is possible to blend a deodorizing material, an odor eliminating material, a substance having bactericidal properties, a coloring substance, and a substance that can provide other effects without inhibiting water absorbability.

(2) Coating Layer Portion

The primary purpose of providing the coating layer portion is to demonstrate an action of causing grains of the water absorbing material wet with excretion such as urine when used to adhere to each other so as to form an aggregate. In the case where the granular core portion is originally colored, the second purpose of providing the coating layer portion is to hide the color of the granular core portion before use by coating the periphery thereof.

The coating layer portion is composed of a substrate and an excretion test material.

<Substrate>

The role for achieving the purposes of the coating layer portion is played by the substrate. As for the materials thereof it is preferable to use, for example, an absorbent material, a water soluble material having adhesion (hereinafter referred to as a "water soluble adhesive material"), a mixture of both materials, or a mixture of paper dust.

As these substances, known substances that do not inhibit testing when carrying out testing of excretion are usable. Usable examples of the absorbent material include CMC (carboxymethyl cellulose), polyvinyl alcohol (PVA), starch (T-pregelatinized starch, dextrin, wheat starch, potato starch), and like materials having water absorbability.

Examples of the water soluble adhesive material include starch adhesives, sodium polyacrylate, and like highly absorbent materials. Usable as a starch adhesive that functions as such an adhesive are starches such as potato starch, wheat starch, sweet potato starch, corn starch (that does not inhibit testing), tapioca starch, rice starch, dextrin, and gelatinized (a) forms of these starches, acrylamide, PVA, carboxymethylcellulose, and sodium alginate, and two or more of these materials are usable in combination.

Examples of paper dust include virgin pulp, toilet paper, toilet paper wastes, tissue paper, tissue paper wastes, cleaning paper, cleaning paper wastes, cellulose wadding, cellulose wadding wastes, paper towel, paper towel wastes, cotton-like pulp, cotton-like pulp wastes, paper dust generated in non-woven fabric production, and a mixture of pulverized products of two or more of these materials. All these materials are used after being pulverized into particulates having a particle size of 0.5 millimeters or less, and preferably 0.3 millimeters or less.

<Excretion Test Material>

The excretion test material is a material in which an ink composition containing a test indicator (hereinafter referred to as a "test indicator-containing ink composition") is adsorbed on a porous adsorbent.

(Test Indicator-Containing Ink Composition)

The test indicator-containing ink composition is a composition in which a test indicator is fixed to an ink composition.

Test Indicator

In the measuring of the pH value of excretion, the pH value of urine is detected and, for example, persistent aciduria or alkaluria is detected, and a purpose of the measurement is to judge necessity of treatment of lithiasis or other diseases. Since the pH value of urine of a healthy carnivore such as a dog or a cat is 4.3 to 7.0, a pH value less than 4.3 when diseased or a pH value greater than 7.0 when diseased can be identified by color change relative to a pH value of 4.3 to 7.0 when normal (when healthy), or that is, use of a urinary pH value test indicator that undergoes color change at the threshold pH value of 4.3 or 7.0 allows identification thereof.

Also, since the pH value of human urine is 4.6 to 7.5 in a healthy person who eats ordinary meals, a pH value of 4.6 to 7.5 when healthy and a pH value less than 4.6 when diseased or a pH value greater than 7.5 when diseased can be identified by color change, or that is, use of a urinary pH value test indicator that undergoes color change at the threshold pH value of 4.6 or 7.5 allows identification thereof.

Examples of urinary pH value test indicators having a color change range at such a pH value, i.e., within the pH range of about 4.5 to 7.7 include thymol blue, phenolphthalein, tropaeolin OOO, cresol red, phenol red, neutral red, bromothymol blue, bromocresol purple, bromophenol red, p-nitrophenol, methyl red, bromocresol green, tetrabromophenol blue, chlorophenol red, methyl orange, ethyl orange, bromophenol blue, brilliant yellow, congo red, bromocresol blue, and the like, and therefore, depending on the purpose of detection, the aforementioned indicators can be used singly or as a combination of two or more indicators.

In particular, in the case where the color change threshold is at a pH value of 4.3, it is preferable to use bromphenol blue or methyl orange and bromocresol green dissolved in ethanol, and in the case where the color change threshold is at a pH value of 7.0, it is preferable to use bromthymol blue.

A universal indicator with which a pH value can be measured throughout the entire pH range can also be used.

Ink Composition

The test indicator-containing ink composition is a composition in which a test indicator and a binder are fixed to a known ink composition. In the present embodiment, it can be prepared by, for example, dispersing or dissolving the urinary pH value test indicator and at least one of cellulose and derivatives of the cellulose (hereinafter collectively referred to as "cellulose") in an organic solvent. Specifically, varnish, hydroxypropylcellulose, or the like that is a type of cellulose is added to the indicator and the mixture is dispersed or dissolved in an organic solvent, e.g., an alcohol such as methanol or ethanol, an aromatic hydrocarbon such as toluene, an ester such as propyl acetate, or the like to form the test indicator-containing ink composition.

For cellulose, preferable are cellose, methylcellulose, ethylcellulose, hydroxypropylcellulose, hydroxypropylmethylcellulose, carboxymethylcellulose, and the like in terms of wettability and ease of visual determination. In this case, as a solvent, it is preferable to select a solvent that can stably dissolve or disperse the test indicator and a resin that serves as the binder.

As binders, there are water soluble polymer compounds that do not affect testing of excretion, that do not prevent color production of the test indicator, and that stabilize the produced color (natural hydrophilic polymer compounds, semisynthetic hydrophilic polymer compounds) as well as water insoluble polymer compounds that do not affect testing of excretion, that do not prevent color production of the test indicator, and that function to form a film. It is preferable to use both types of binder in combination.

Usable examples of the natural, hydrophilic polymer compounds include sweet potato starch, potato starch, arum root powder, funori seeweed, sodium alginate, *Abelmoschu manihot*, tongaro gum, gum arabic, dextran, levan, nikawa glue, gelatin, casein, collagen, and the like.

Usable examples of the semisynthetic hydrophilic polymer compounds include methylcellulose, hydroxypropylcellulose, hydroxyethylcellulose, carboxymethylcellulose, and like cellulosic derivatives, dialdehyde starch derivatives, and the like.

Usable examples of the water insoluble polymer compounds that function to form a film include nitrocellulose, cellulose acetate, ethylcellulose, cellulose acetate butyrate, and like cellulosic resins as well as polyester resin, alkyd resin, polyurethane resin, epoxy resin, acrylic resin, vinyl chloride resin, vinyl chloride copolymer resin, polyvinyl butyral, polyvinyl acetate emulsion, vinyl acetate copolymer (such as vinyl acetate-acrylic ester) emulsion, acrylic ester copolymer emulsion, epoxy resin emulsion, synthetic rubber latex, and the like. Among these polymer compounds that function to form a film, urethane resin and polyvinyl butyral, in particular, do not adversely affect the color change of the test indicator or the measurement of a pH value, and are thus preferable.

Moreover, known additives such as binders, stabilizers, or surfactants that enable formation of a uniform reagent layer (nonionic surfactants, anionic surfactants, cationic surfactants, amphionic surfactants, polyethylene glycol, or the like) can be added to the test indicator-containing ink composition.

Generally, the components of the test indicator-containing ink composition and their contents are as follows: indicator 1 wt % to 3 wt %, cellulose 1 wt % to 5 wt %, adhesive 10 wt % or less, with the remainder being composed of a solvent.

(Porous Adsorbent)

For the porous adsorbent, it is necessary to use an adsorbent including a large number of micropores (fine apertures) and having a large surface area and an adsorbance of 25 wt % or greater. It is possible to use known substances such as silica gel (so-called type A silica gel and type B silica gel) (silicon dioxide) and zeolite (aluminosilicate). In particular, type B silica gel (an average absorbing surface area of about 450 ($m^2/g$), an average micropore size of about 60 Å, a micropore volume of about 0.75 (ml/g)) has a larger micropore size and a larger micropore volume than type A silica gel (an average absorbing surface area of about 700 ($m^2/g$), an average micropore size of about 24 Å, a micropore volume of about 0.46 (ml/g)), and thus demonstrates a high level of adsorbability when adsorbing the test indicator-containing ink composition and is thus highly preferable.

Also, a penetrating agent or a swelling agent can be added to the coating layer portion. As the penetrating agent, known substances such as various surfactants can be used, and as the swelling agent, known substances such as cellulose-based swelling agents can be used.

<Other Additives>

In the case where particles of a ground product of non-woven fabric are used in the water absorbing material of the present invention, the particles of the ground product adhere to each other and form an aggregate when excretion is discharged. Therefore, in order to make it easy to handle the excretion treating material after discharging, an adhesive that is a starch adhesive having adhesion and not affecting testing of urine is added. As such an adhesive, water soluble polymer compounds such as natural hydrophilic polymer compounds and semisynthetic hydrophilic polymer compounds for use as a binder in the test indicator-containing ink composition can be used.

Also, a penetrating agent or a swelling agent can be added to the coating layer portion. As the penetrating agent, known substances such as various surfactants can be used, and as the swelling agent, known substances such as cellulose-based swelling agents can be used.

Proportions of Respective Materials

It is most preferable that the present water absorbing material has proportions of its components of 80 wt % to 87 wt % of the granular core portion and 20 wt % to 13 wt % of the coating layer portion in connection with the size of the granular core portion, the thickness of the coating layer portion, and the proportion of water soluble dye added, which will be described below.

The coating layer portion is composed of 90 wt % to 96 wt % of a substrate and 10 wt % to 4 wt % of an excretion test material.

It is necessary that the test indicator in the excretion test material is added in an amount of 0.015 wt % to 0.10 wt % relative to the total amount of the coating layer portion. Therefore, when the test indicator is fixed to an ink composition, it is necessary to adjust the amounts of the solvent and other components such that the amount of the test indicator is within the aforementioned range and to determine the amount of the porous adsorbent according to the type thereof.

[Production Method]

Next, the method for producing a water absorbing material of the present invention is described in reference to FIG. 1.

The method for producing an excretion treating material of the present invention includes a granulation step (S1), an excretion test indicator adsorption step (S2), a coating material production step (S3), a coating step (S4), a classification step (S5), and a drying step (S6).

(1) Granulation Step (S1)

This step is for forming a granular core portion.

In this step, components such as pulp wastes are pulverized with a crusher so as to have a specific size, and the pulverized components are placed in a mixer and mixed such that specific proportions are attained. Then, water is added to increase the moisture content, and then the mixed components are subjected to extrusion granulation. In this manner, a granular core portion forming operation is performed.

The coating material adheres to the periphery of the granular core portion due to moisture present in the granular core portion. Therefore, when the moisture content of the granular core portion before formation of the coating layer portion is less than the lower limit, the materials that form the coating layer portion do not adhere to the periphery of the granular core portion. That is, when the moisture content of the granular core portion is less than 20 wt %, the coating layer portion, which has a specific thickness necessary for demonstrating a specific action, is not formed, and as a result, no multilayer water absorbing material is formed, separation of the coating layer portion occurs, no aggregate is created after use, and the appearance is poor. Therefore, such a moisture content is not preferable.

On the other hand, when the water content of the granular core portion exceeds 41 wt %, moisture of the granular core portion excessively leaches out into the coating layer portion during the formation of the coating layer portion, and thus moisture comes into contact with the test indicator and the test indicator produces color. Therefore, such a moisture content is not preferable.

Accordingly, in the case of performing the aforementioned extruding granulation, it is preferable to adjust the moisture content of the granular core portion so as to be 20 wt % to 41 wt % (more preferably 20 wt % to 25 wt %).

(2) Excretion Test Indicator Adsorption Step (S2)

This step is for preparing an excretion test material.

This step is for allowing a test indicator-containing ink composition produced by dissolving the test indicator in a solvent to be adsorbed on a porous adsorbent.

In this step, a test indicator-containing ink composition produced by a known method is added dropwise little by little to, and is blended with, a porous adsorbent that has been processed into fine powder in order to allow the test indicator to be adsorbed on the porous adsorbent to prepare an excretion test material.

The proportions of the test indicator and the porous adsorbent are determined according to the adsorbance of the porous adsorbent. However, when the amount of the porous adsorbent added exceeds a specific amount, particles of the porous adsorbent are exposed from the surface layer of the coating layer portion, and thus such exposed portions project from the surface layer in the form of protrusions. Then, grains of the water absorbing material are brought into contact with each other during packaging and transportation, and thus the projecting portions separate from the base portions, creating a condition where, for example, a damaged surface layer portion is present. Therefore, such an amount is not preferable.

It is necessary that the test indicator is added in an amount of 0.015 wt % to 0.10 wt % relative to the total amount of the coating layer portion, and when the test indicator is fixed to the ink composition, the amounts of the solvent and other components are adjusted such that the test indicator is within the aforementioned range. Meanwhile, since every porous adsorbent has its own largest adsorbance, the minimum required amount of the porous adsorbent is determined so as to allow a necessary test indicator to be adsorbed thereon, and therefore the test indicator-containing ink composition is adsorbed on the porous adsorbent of the amount thus determined.

(3) Coating Material Production Step (S3)

This step is for producing a coating material constituting the coating portion. This step is for producing a coating material by adding the excretion test material prepared in the excretion test indicator adsorption step to a substrate composed of specific materials and mixing them in specific proportions so as to attain the desired amount of the test indicator.

Note that addition of desired materials such as a penetrating agent and a swelling agent other than the coating material and the excretion test material to the coating layer portion is carried out in this step.

(4) Coating Step (S4)

This step is for forming the coating layer portion by coating the periphery of the granular core portion with the coating material. In this step, the coating material is sprayed around the granular core portion using a coating device or the like to form the coating layer portion. In this manner, an operation for producing a multi-layer water absorbing material is performed.

(5) Classification Step (S5)

This step is for classifying particles of the water absorbing material so as to have a specific size.

In this step, the water absorbing material produced in the previous step is sifted with a sieve having a specific mesh size to separate products that do not have a specific size. In this manner, an operation for obtaining only the products that have a specific size is performed.

(6) Drying Step (S6)

This step is for drying the obtained water absorbing material having a specific size using a dryer.

In the case where the moisture content of the granular core portion is high during storage of the water absorbing material, moisture of the granular core portion leaches out for an extended period of time, thus reacting with the test indicator, and color is produced. Therefore, the water absorbing material is dried such that the water content of the granular core portion is 3% or greater and 10% or less, which enables prevention of color production during storage.

[Functional Effects]

Regarding the water absorbing material of the present invention, a test indicator is not directly added to the components of the coating layer portion, but the test indicator is first dissolved in a solvent and processed into a test indicator-containing ink composition, and then adsorbed on a porous adsorbent. The porous adsorbent has the test indicator-containing ink composition adsorbed in its gap portions, and therefore, leaching of moisture from the granular core portion or the like can be blocked to some extent, and if apertures are present in the gap portions, the gap portions can retain moisture, and it is therefore possible to prevent the highly reactive test indicator from producing color, which is caused by the reaction of the test indicator, before use. Since the test indicator is blended in the coating layer portion, the coating layer portion promptly undergoes color change because it is in contact with the test indicator, and it is thereby possible to readily determine a test result in a short period of time.

So far, one preferable embodiment has been described, but the present invention is not limited to that embodiment, and design modifications can be suitably performed without departing from the scope of the present invention. In the present embodiment, a description has been provided using as an example a water absorbing material for pets for treating excretion. Needless to say, however, the water absorbing material may be applied to humans and other animals.

In addition, a description has been provided using a urinary pH value detection indicator as an example of the test indicator, but the test indicator is not limited thereto, and urinary glucose detection indicators, urinary protein detection indicators, urinary occult blood detection indicators, urinary urobilinogen detection indicators, or like various indicators are usable.

Moreover, in the description provided above, the excretion test indicator adsorption step has been described as being performed after the granulation step, but these steps may be performed chronologically in parallel, and in addition to the aforementioned steps, other steps may be suitably added.

If a plurality of different types of test indicators are dissolved in a solvent and adsorbed on a porous adsorbent, and the mixture is added to a coating layer portion, multiple test results can be determined at once.

EXAMPLES

To investigate the performance of the water absorbing material of the present invention, samples were prepared according to the production method described below, and a color production test was carried out.

<Components>

Each sample used in the following test was produced according to the production method of the present invention, and was a multi-layer water absorbing material composed of a granular core portion and a coating layer portion. The weight ratio between the materials constituting the granular core portion and the coating layer portion was 83 wt % to 17 wt %, and a 1000 g sample was produced.

(1) Granular Core Portion

Ingredients were virgin pulp (50 wt %, a water content of 8.0%), pulp sludge (49 wt %, a water content of 57.0%), and cornstarch (1 wt %, a water content of 9.0%).

(2) Coating Layer Portion

The coating layer portion was prepared by mixing a substrate (a mixture of virgin pulp and carboxymethylcellulose) (provided that their mixing ratio in wt % was the same) and an excretion test material The excretion test material was composed of a test indicator-containing ink composition and a porous adsorbent.

As the test indicator-containing ink composition, a composition prepared by dissolving bromothymol blue (a test indicator) (manufactured by Advantec Toyo Co., Ltd.) and a cellulose-based resin in an organic solvent (industrial ethyl alcohol and methyl alcohol) was used (both manufactured by Toyo Ink MFG. Co., Ltd.), and samples were produced with varying amounts of the test indicator added.

Fine powder of silica gel (B type) (manufactured by Hymo Co., Ltd.) was used as the porous adsorbent.

<Samples>

The coating layer portion had either 96 wt % of a substrate and 4 wt % of an excretion test material or 90 wt % of a substrate and 10 wt % of an excretion test material relative to the total weight.

Then, in either case, within the range of the aforementioned excretion test material content, the amount of the test indicator was changed by 0.005 wt % while satisfying the range of 0.005 wt % to 0.11 wt % relative to the total amount of the coating layer portion to adjust the amount of the ink composition blended, thus preparing a total of 44 samples having different blending proportions.

<Observation Results>

Regarding each of the samples above, the extent of color production of the coating layer portion before and after use was visually inspected. As a result, no color production by the coating layer portion was visible in the samples before use that had the amount of the test indicator added relative to the total weight of the coating layer portion of 0.015 wt % to 0.10 wt %. Then, when a suitable amount of mock urine having a pH of 6.8 was added dropwise (corresponding to a sample after use), light green color was exhibited, and when a suitable amount of mock urine having a pH of 8.0 was added dropwise, blue color was exhibited, thus providing favorable results (the same results were obtained also when the proportions of the substrate and the excretion test material were different).

On the other hand, regarding the samples in which the amount of the test indicator added relative to the total weight of the coating layer portion was 0.005 wt % and 0.010 wt %, both before use and when mock urine similar to that described above was added dropwise (corresponding to a sample after use), no clear color change was identified, thus failing to give favorable results.

Also, regarding the samples in which the amount of the test indicator added relative to the total weight of the coating layer portion was 0.105 wt % and 0.11 wt %, green color appeared on the coating layer portion before use, thus failing to give favorable results (the same results were obtained also when the proportion between the substrate and the excretion test material was different).

According to the results presented above, it is clear that the amount of the test indicator added needs to be within the range of 0.015 wt % to 0.10 wt % relative to the total amount of the coating layer portion.

REFERENCE SIGNS LIST

S1 Granulation step
S2 Excretion test indicator adsorption step
S3 Coating material production step
S4 Coating step
S5 Classification step
S6 Drying step

The invention claimed is:

1. A method for producing a multi-layer water absorbing material comprising a granular core portion for absorbing moisture from outside and a coating layer portion coating the granular core portion, the coating layer portion containing an excretion test indicator being a reagent that changes its color upon reaction with excretion, the method comprising:

a granulation step of producing the granular core portion, an excretion test indicator adsorption step of dissolving the excretion test indicator in a solvent for dissolving the excretion test indicator and allowing the dissolved excretion test indicator to be adsorbed on a porous adsorbent having an adsorbance of 25 wt % or greater and including micropores, a coating material production step of adding the excretion test indicator adsorbed, by the excretion test indicator adsorption step, on the porous adsorbent to a substrate to produce a coating material that constitutes the coating layer portion, and a coating step of coating the granular core portion with the coating material.

2. The method for producing the water absorbing material according to claim 1, wherein the substrate has a function of causing grains of the water absorbing material which grains are wet with excretion to adhere to each other so as to form an aggregate.

3. The method for producing the water absorbing material according to claim 1, wherein the substrate hides a color of the granular core potion before use.

4. The method for producing the water absorbing material according to claim 1, wherein the porous adsorbent is type B silica gel.

5. The method for producing the water absorbing material according to claim 1, wherein a plurality of different types of the excretion test indicators are dissolved in the solvent and the dissolved excretion test indicators are adsorbed on the porous adsorbent in the excretion test indicator adsorption step.

6. The method for producing the water absorbing material according to claim 1, wherein the coating step of coating a periphery of the granular core portion.

7. The method for producing the water absorbing material according to claim 5, wherein the plurality of different types of the excretion test indicators include at least two from the group consisting of a urinary pH value detection indicator, a urinary glucose detection indicator, a urinary protein detection indicator, a urinary occult blood detection indicator, and a urinary urobilinogen detection indicator.

* * * * *